(12) United States Patent
Hjortfors et al.

(10) Patent No.: US 11,623,171 B2
(45) Date of Patent: Apr. 11, 2023

(54) FILTER SYSTEM COMPRISING A LAYER WITH ACTIVE ADSORBENT CONTAINING BAGS

(71) Applicant: ABSOLENT AB, Lidköping (SE)

(72) Inventors: Jan Hjortfors, Skara (SE); Anders Knutsson, Järpås (SE); Joel Svanström, Lidköping (SE); Jan Berndtsson, Kvänum (SE)

(73) Assignee: ABSOLENT AB, Lidköping (SE)

( * ) Notice: Subject to any disclaimer, the term of this patent is extended or adjusted under 35 U.S.C. 154(b) by 329 days.

(21) Appl. No.: 16/650,992

(22) PCT Filed: Oct. 1, 2018

(86) PCT No.: PCT/SE2018/051000
§ 371 (c)(1),
(2) Date: Mar. 26, 2020

(87) PCT Pub. No.: WO2019/066715
PCT Pub. Date: Apr. 4, 2019

(65) Prior Publication Data
US 2020/0276533 A1 Sep. 3, 2020

(30) Foreign Application Priority Data
Oct. 1, 2017 (SE) .................... 1730271-2

(51) Int. Cl.
*B01D 46/00* (2022.01)
*B01D 46/02* (2006.01)
*B01J 20/28* (2006.01)

(52) U.S. Cl.
CPC ..... *B01D 46/0036* (2013.01); *B01D 46/0038* (2013.01); *B01D 46/023* (2013.01); *B01J 20/2805* (2013.01)

(58) Field of Classification Search
CPC ........... B01D 46/0036; B01D 46/0038; B01D 46/023; B01J 20/2805
See application file for complete search history.

(56) References Cited

U.S. PATENT DOCUMENTS

| | | | | |
|---|---|---|---|---|
| 3,871,849 A | * | 3/1975 | Smith ................... | B01D 46/12 |
| | | | | 55/491 |
| 2003/0217640 A1 | * | 11/2003 | Alper ................. | B01D 46/0036 |
| | | | | 96/154 |
| 2017/0095771 A1 | * | 4/2017 | Venet ................... | B01D 46/44 |

FOREIGN PATENT DOCUMENTS

| | | |
|---|---|---|
| EP | 0517021 A1 | 12/1992 |
| GB | 2 063 095 A | 6/1981 |

OTHER PUBLICATIONS

International Search Report dated Dec. 18, 2018, corresponding to International Application No. PCT/SE2018/051000.

* cited by examiner

*Primary Examiner* — Henry T Crenshaw
(74) *Attorney, Agent, or Firm* — Ladas & Parry LLP; Malcolm J. MacDonald, Esq.

(57) ABSTRACT

A filter system for adsorbing an odor of a gas flow in an industrial process includes a filter module (1) with a layer (11) containing active adsorbent (3). The layer (11) includes a plurality of active adsorbent containing permeable bags (2) arranged in close proximity to each other.

11 Claims, 4 Drawing Sheets

FILTER SYSTEM COMPRISING A LAYER WITH ACTIVE ADSORBENT CONTAINING BAGS

TECHNICAL FIELD

The present invention concerns gas filtering in an industrial process plant. More precisely the invention concerns adsorption of molecules in a gas stream. In particular the invention concerns an odour-removing filter within the process industry.

BACKGROUND OF THE INVENTION

There are known great many solutions for gas particles filtration within industrial processes. This includes systems for filtering oil mist or oil smoke as well as dust. However when it comes to removing gas molecules such as odour not so many solutions are known. For filtering odour or poisonous molecules from a process gas mainly three methods are feasible; adsorption, condensing or oxidation. Condensing comprises chilling the gas into liquid phase. Oxidation comprises catalytic combustion by an open flame. Mostly an adsorbent like active carbon is used to adsorb the odour from the gas. However metal oxides like copper oxide and alumina oxide may be a more effective adsorbent than carbon for certain molecules.

Adsorption is the adhesion of atoms, ions or molecules from a gas, liquid or dissolved solid to a surface. This process creates a film of the adsorbate on the surface of the adsorbent. It differs from absorption in which a fluid is dissolved by a liquid or solid. Adsorption is a surface-based process while absorption involves the whole volume of the material. However having adsorbed a certain amount of gas molecules the adsorbent will be saturated. When saturated the adsorbent must be replaced by a fresh adsorbent. Therefore the adsorbent must be easy to replace.

In providing an adsorption filter great care must be taken to make the gas evenly passing the adsorbent. Often the adsorbent comprises a compact layer of active carbon particles on a tray. The carbon is encapsulated by a woven tissue or the like to hold it in place. The trays are positioned horizontally in a housing with spaces in between. Every second such space is open to an upstream side of the gas flow. Every other space is open to a downside side of the gas stream to let out the cleaned gas. The main gas stream in such a filter is thus horizontal. Hence the gas stream enters the first set of spaces, turn transversely through the filter layers to the second set of spaces, turn back transversely and out of the filter.

Already in the design of these filters there is an obvious problem of providing a long-lasting seal between the upstream side spaces from the downstream side spaces. To be efficient all gas must pass the active carbon and not slip around the trays. Hence the trays must have a seal all around the trays while still being able to be removed for inspection and refill. In known filters the gas flow may not be uniform through the filter layers. Since there might be an uneven pressure profile in the upstream side of the trays also the flow will be affected. Hence the activated carbon will be saturated at the upstream side of the tray while the other side will still contain active carbon. This leads to the whole carbon layer having to be exchanged prematurely. Thus for creating a long lasting active carbon filter great care must be taken to create a gas flow such that no parts of the active carbon layer is saturated prior to other parts.

Saturated active carbon is wasted and must be replaced. Commonly the trays containing the wasted active carbon are sent to a refilling facility where the active carbon containing trays are recycled. Waste carbon from the dismantled trays is pored out in a pile in the back yard. Then the tray is relined and filled with new active carbon from a pile next to the first pile. It is known the trays being dismantled into parts where metal and tissues are sent to different locations for recirculation. This is a cumbersome and dirty work. Thus known methods do not contain a full recycling circle. Besides, the process involves a plurality of work stations. Also the plurality of transports to and from the recycling facilities does not result in an effective recycling process.

For recycling purposes the trays are built up far too complicated for an effective dismantling into recyclable parts. Except for the wasted carbon there is a plurality of sheets, scrims and woven textures which has to be taken care of separately. Often the wasted carbon is simply separated from the trays and transported for combustion. The tray and its content may often provide heavy loads. Exchanging such a tray may require more than one person or the need for a lifting aid.

From EP 517021 an air filter for cars and electronic devices is previously known. The filter material is contained between air-permeable tube formed covers. The object of the filter is to provide an air filter with a simplified design and a variable use. In addition the filter should be easier to dispose. The air filter is formed by a series of fabric tubes which are closed at both ends by closing means. The filter tubes are filled with pulverulent, granular or the like filter material, in particular with activated charcoal. The fabric tubes are composed of a material which lets through the air to be cleaned but which holds back the filter material. They are arranged in parallel next to each other only separated by connection lines. Thus they are firmly attached to each other by the connection lines to form a flexible filter.

In production the filter is provided from two filter mats forming channels separated by connection lines (FIG. 6). The channels between the connection lines are filled with filtering material and plugged at each end. By the filling the channels assume a cylindric shape and become formally stable in their axial directions. Thus the filter mat becomes stiff in one direction but flexible in the other direction. The filtering efficiency is somewhat incomplete since the layer of filtering material is not evenly thick and the connecting lines allows air to pass without coming into contact with the filter material.

From U.S. Pat. No. 3,871,849 a disposable active carbon filter is previously known. The object of which is to prevent the deleterious effects of settling of the filter material. Accordingly the disposable carbon filter comprises at least one paperboard carton containing granular activated carbon compressively contained by a porous scrim material. More specifically the carbon filter comprises at least one six-sided carton tray to be stacked in a filter assembly divided into chambers. When the carbon filter beds are spent trays may be removed through these chambers for disposal.

The known filter provides a disposable carbon filter comprising at least one six-sided paperboard carton including a pair of opposed parallel panels having cutaway sections, defining opposed flow-through apertures therein, for the ingress of dirty air to be treated and the egress of clean air after treatment; and, a fluid pervious scrim material disposed within the paperboard carton across the flow-through apertures to compressively contain activated carbon particles.

The flow of gas to be purified is in the longitudinal direction. Such an arrangement requires that the gas be directed through the trays at right angles to the direction at which it enters the housing. It is therefore necessary to change direction of the gas within the housing. To accomplish such a change it is required that the alternate ends of successive carbon filter trays be connected to fluid impervious plate means to define gas receiving and gas expelling chambers. Such chambers are arranged parallel to the direction of gas flow through the housing so that the gas flowing into the gas receiving chambers flows into one end thereof, changes direction by 90 degrees to pass through a filter tray, comprising either the top or bottom surface of the chamber, and finally changes direction back by 90 degrees to pass out of the housing through an expelling chamber.

Each of the cartons is lined with a porous scrim material and then completely filled with activated granular carbon particles. A second layer of porous scrim or other fluid pervious covering is then laid over the carbon particles in compressive fashion and a precut facing of sheet material having a flow through orifice is laid thereover to form a carbon holding cavity containing the activated granular carbon particles under compression. In an embodiment the carton contains a plurality of porous scrim bags containing carbon arranged side by side.

From GB 2063095 an odour-removing filter is previously known. The object is to provide a filter having economically recoverable material for further use. The filter comprises a net stocking which is divided by suitable stitching into separate pockets each containing particles of odour-removing material such as active carbon. The stocking may be cur to enable the filter material to be poured out for processing and reuse.

The pockets are separated by grooves provided by parallel seams or stitches. The grooves are aimed to receive members of a frame to hold the filter in place. Unfortunately these grooves provide air passages where the gas will not come into contact with the odour-removing filter material.

SUMMARY OF THE INVENTION

A primary object of the present invention is to seek ways to improve an odour-removing filter for the process industry.

This object is achieved according to the invention by a filter system characterized by the features in the independent claim 1 or by a method characterized by the steps in the independent claim 7. Preferred embodiments are described in the dependent claims.

According to the invention the odour-removing filter comprises a layer of an active adsorbent arranged perpendicular to the main gas stream. The layer of active adsorbent particles comprises a plurality of permeable flexible containers allowing the gas to pass but keeping the active adsorbent. In an embodiment of the invention the flexible container comprises a bag. By the expression "bag" is understood a formable enclosure with aperture at one end. A bag has no determined envelope surface. Thus a bag containing granular material can be formed to fill whatever shape of a receiving cavity. The active adsorbent filled bags are arranged close to each other to completely fill out the receiving cavity. In an embodiment the layers are perpendicular to the air flow. By the flexible structure of the bags the layers of flexible bags containing active adsorbent can be assembled very tight and consequently no air will pass without coming into contact with the adsorbent. In an embodiment the flexible container comprises a sack which is a coarse weave storage device with one end opening.

In an embodiment the bags are arranged side by side in close proximity on a carrier in a housing receiving the gas. By arranging the gas flow perpendicular to the active adsorbent layer the pressure profile will be even and thus also the gas flow. By encapsulating the adsorbent in bags a great variety of filters may be built. The bags are easy to handle, easy to use in filters and easy to deposit or reactivated. In an embodiment the adsorbent comprises active carbon. In an embodiment the adsorbent comprises a metal oxide.

The bag comprises a gas permeable material yet providing a flexible closed container for keeping the active adsorbent. By providing the adsorbent in bags a clean environment is secured. Besides, the adsorbent bags are light weighted and may be handled by a single person without the help of other equipment. Thus a person may perform an exchange of saturated adsorbents of his own and without being polluted by adsorbent.

In an embodiment of the invention the bags are arranged closed to each other in a layer on a diffuser. The diffuser comprises a stiff means for carrying the bags and means for an even distribution of the gas. The presence of a diffuser provides an even gas distribution through the layer of bags. In an embodiment the diffuser comprises a grid. In an embodiment the diffuser comprises a sheet of metal or plastic having a plurality of passageways for the gas. In an embodiment a second layer of active adsorbent containing bags is arranged on a second diffuser in the housing. In this second layer the bags may be arranged in parallel with the first layer. However the arrangement of bags in any direction may be sufficient. In an embodiment the second layer is arranged at a distance to the first layer. A cavity is thus formed between the layers of bags. In the cavity a turbulent gas flow is created and thus an even pressure profile. In an embodiment the diffusors comprises a curved form and the bags being stabilized by a backbone structure of a stiff material such as a mesh of coarse material.

The adsorbent containing bags are conveniently provided from a woven tissue. In an embodiment they are made of natural fibers and having closed ends provided by stitching. In an embodiment the bags are made of plastic fibers. In an embodiment the tissue material comprises heat resistant material. This enables wasted adsorbents to be reactivated while contained in the bags.

The housing comprises a cuboid shape and is arranged to become a module in a process filter system. Thus the filter housing may be dismounted from the filter system. The bags containing saturated adsorbents are picked up and sent for reactivation. Bags with active or reactivated adsorbents are packed in the housing and the module is put back in the filter system. The simple design of these modules makes the change go very quickly. In an embodiment the filter module is arranged with the bags packed vertically and the gas flow horizontally. In this embodiment the bags are piled between a first diffuser and a second diffuser.

The number of bags to be placed in the housing depends on the size of the gas flow. Design criteria may be acceptable pressure drop or expected saturation time for the active adsorbent. Often a plurality of bag layers is chosen. Depending on the degree of adsorption efficiency a design aim may be to make the gas stay within the active adsorbent layer for a predetermined time. In an embodiment the predetermined time interval is 0.1-0.5 seconds. In an embodiment a multi layer filter comprises a cavity separating the layers. The cavity provides an even gas stream distribution and an even pressure distribution.

In a recycling system the saturated adsorbent bags are sent to an activation facility. There the waste adsorbent is reactivated while contained in the bags. After reactivation the bag is packed in an air tight container and sent back to the filter user. The container might be a vacuum tight plastic bag. This packing enabled the filter bags to be stored without the active adsorbent being partly saturated by ambient gas.

In a first aspect of the invention the object is achieved by a filter system for adsorbing an odour of a gas flow in an industrial process comprising a filter module with a layer containing an active adsorbent, wherein the layer comprises a plurality of active adsorbent containing permeable bags arranged in close proximity to each other. In an embodiment the filter module comprises a diffuser for spreading the gas flow. In an embodiment In an embodiment the layer comprises a second diffuser. In an embodiment the bags comprises a woven tissue. In an embodiment the filter module comprises a plurality of layers. In an embodiment the filter module comprises a cavity between two layers of bags for smoothing the gas pressure. In an embodiment the layers are arranged perpendicular to the gas flow.

In a second aspect of the invention the object is achieved by a method of adsorbing an odour from a gas flow of an industrial process comprising a filter module with a layer containing active adsorbent, wherein the layer is arranged perpendicular to the gas flow, the active adsorbent is filled in a plurality of permeable bags and the plurality of bags is assembled in close proximity on the layer. In an embodiment the method further comprises providing a plurality of layers of active adsorbent containing bags and forming between two layers a cavity for smoothing the gas pressure between the layers. In an embodiment the permeable bags is formed of a woven tissue.

BRIEF DESCRIPTION OF THE DRAWINGS

Other features and advantages of the present invention will become more apparent to a person skilled in the art from the following detailed description in conjunction with the appended drawings in which.

DESCRIPTION OF PREFERRED EMBODIMENTS

Figure 1:
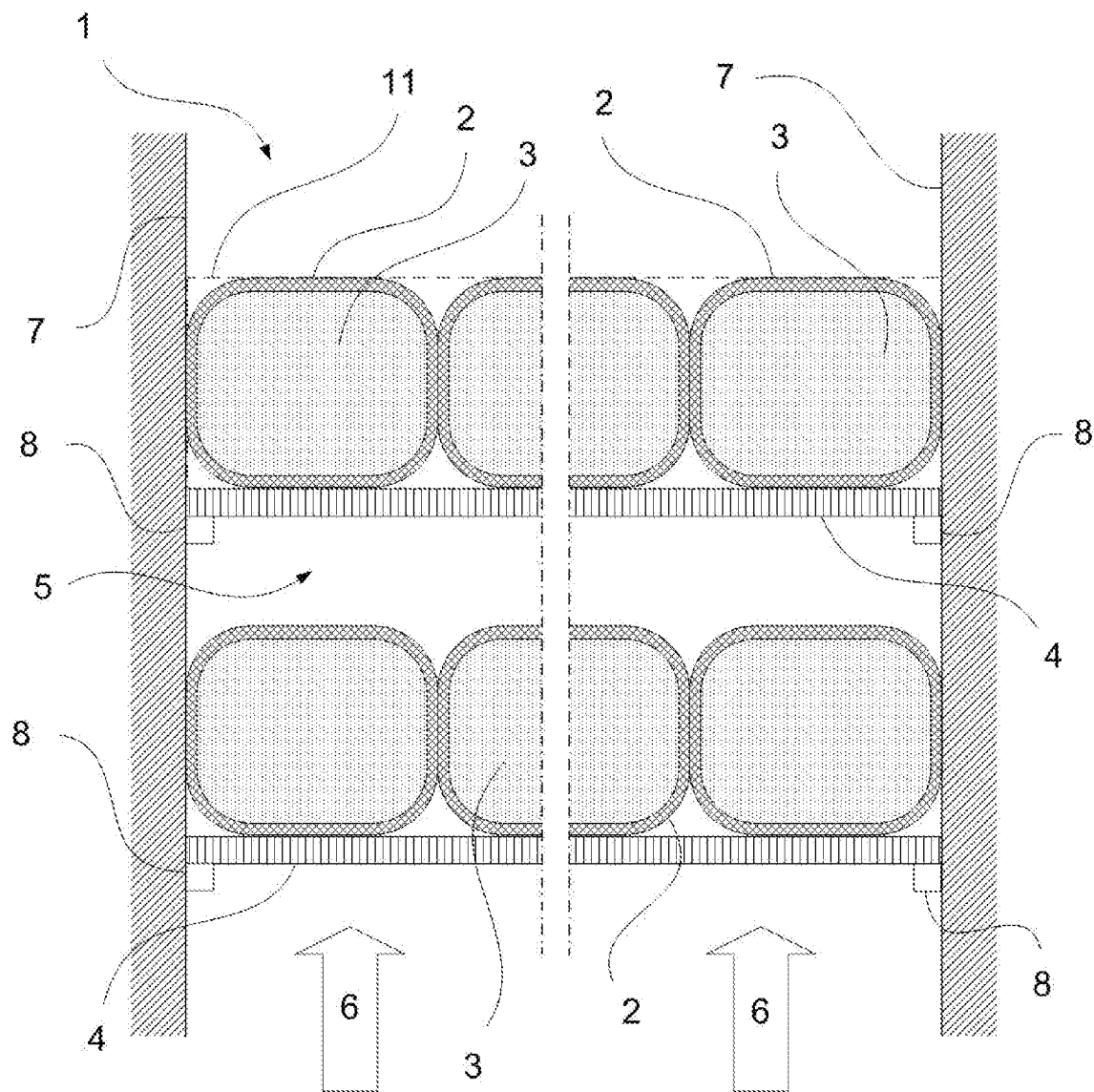
FIG. 1 is a section of a filter module according the invention.

A filter module 1 according to FIG. 1 is arranged to clean a horizontal gas flow 6. The module comprises a plurality of bags 2 containing an active adsorbent 3. The bags are closely arranged side by side in a layer 11 between a first and second wall 7 of the filter module 1 on a diffuser 4 such that the gas flow must pass the active adsorbent containing bags. The diffuser comprises a bag carrying sheet with a plurality of passageways for the gas flow. The function of the diffuser is to evenly distribute the gas flow in order to provide a smooth pressure profile and thus a uniform gas flow. The diffuser is placed on brackets 8 on the walls 7 of the filter module.

In the embodiment shown in FIG. 1 there are two layers 11 of active adsorbent bags. Between the two layers of bags there is formed a cavity 5. This cavity helps the gas flow to a uniform passage of the filter module. The gas having passed the first active adsorbent layer will be spread out and building up an even pressure profile towards the next active adsorbent layer. The probability of each gas molecule to reach an active adsorbent particle is thus increased. By the contact with an active adsorbent particle the odour carried by the gas will be adsorbed by the active adsorbent.

Figure 2:
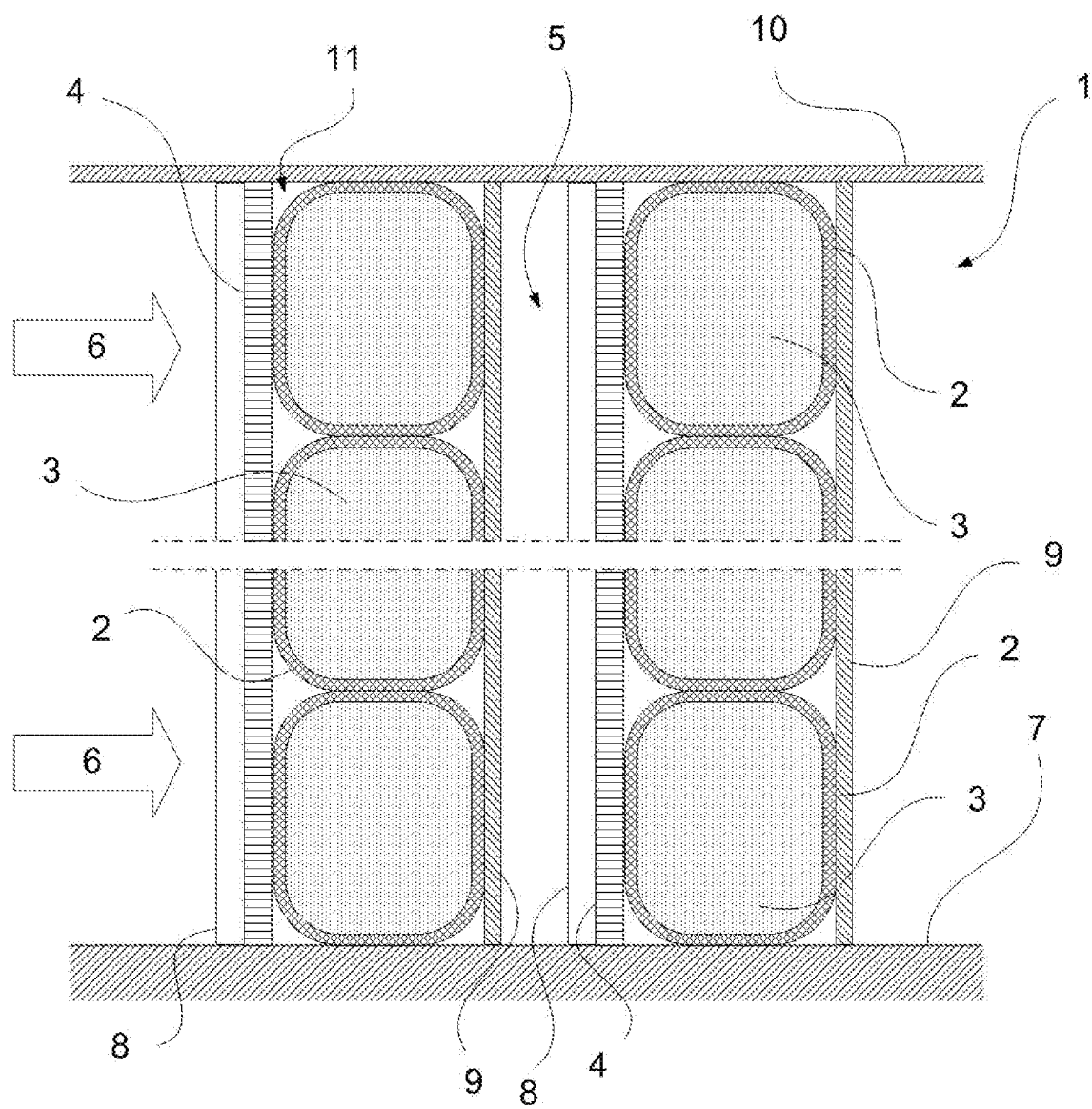
FIG. 2 is a section of a second embodiment of the filter module having a horizontal gas flow according to the invention, FIG. 3 Is an embodiment of a filter module according to the invention.

An embodiment of the filter module is shown in FIG. 2. In this embodiment all figure designations are the same but the gas flow is horizontal. The active adsorbent containing bags are in this embodiment piled in a layer 11 between a first diffuser 4 and a second diffuser 9. In this embodiment the bags are piled vertically between a wall of the filter module and a lid 10 which tightly is enclosing the filter module. Care must be taken to achieve a fully compacted layer of active adsorbent such that no escapeways for the gas arise around the active adsorbent layer.

Figure 3:
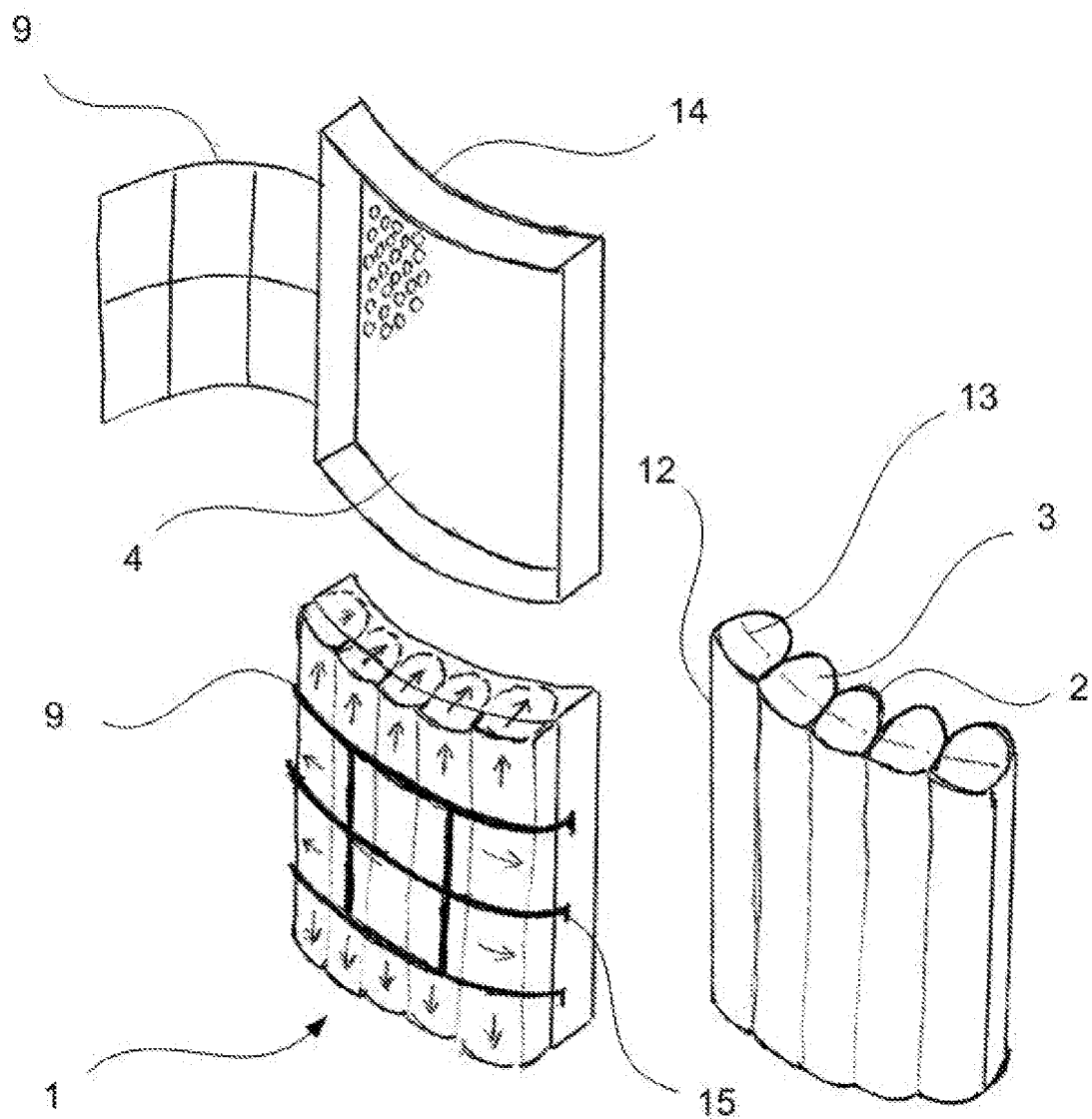

A filter module 1 being a part of a filter system according to an embodiment of the invention is shown in FIG. 3. The filter module 1 comprises a frame 14 including a first diffusor 4. In the embodiment shown the first diffusor comprises a perforated sheet of metal. However any kind of stiff device capable of withstanding pressure yet allowing gas to pass would be sufficient. The frame 14 is arranged to receive a plurality of permeable flexible containers 2 keeping active adsorbent 3. In the embodiment shown the flexible containers comprises bags of active adsorbent such as active carbon. The bags are positioned closely side by side in the frame.

To hold the bags in position the filter module comprises a second diffusor 9 in the form of a grid. In the embodiment shown the grid is hinged on one side of the frame and locked on the opposite side by a locking mechanism 15. For convenient handling of the bags the plurality of bag aimed for the frame is fixed to a backbone 12 bendable along a curve 13. The backbone must be stiff enough to hold the bags in position and simultaneously capable of letting the air pass. One suitable backbone material is a mesh of stiff fibers. In an embodiment of the invention the frame 14 is turned into a horizontal position when the bags are mounted. When finished and closed by the grid 9 it is raised into a vertical position and mounted in the filter module.

Figure 4:
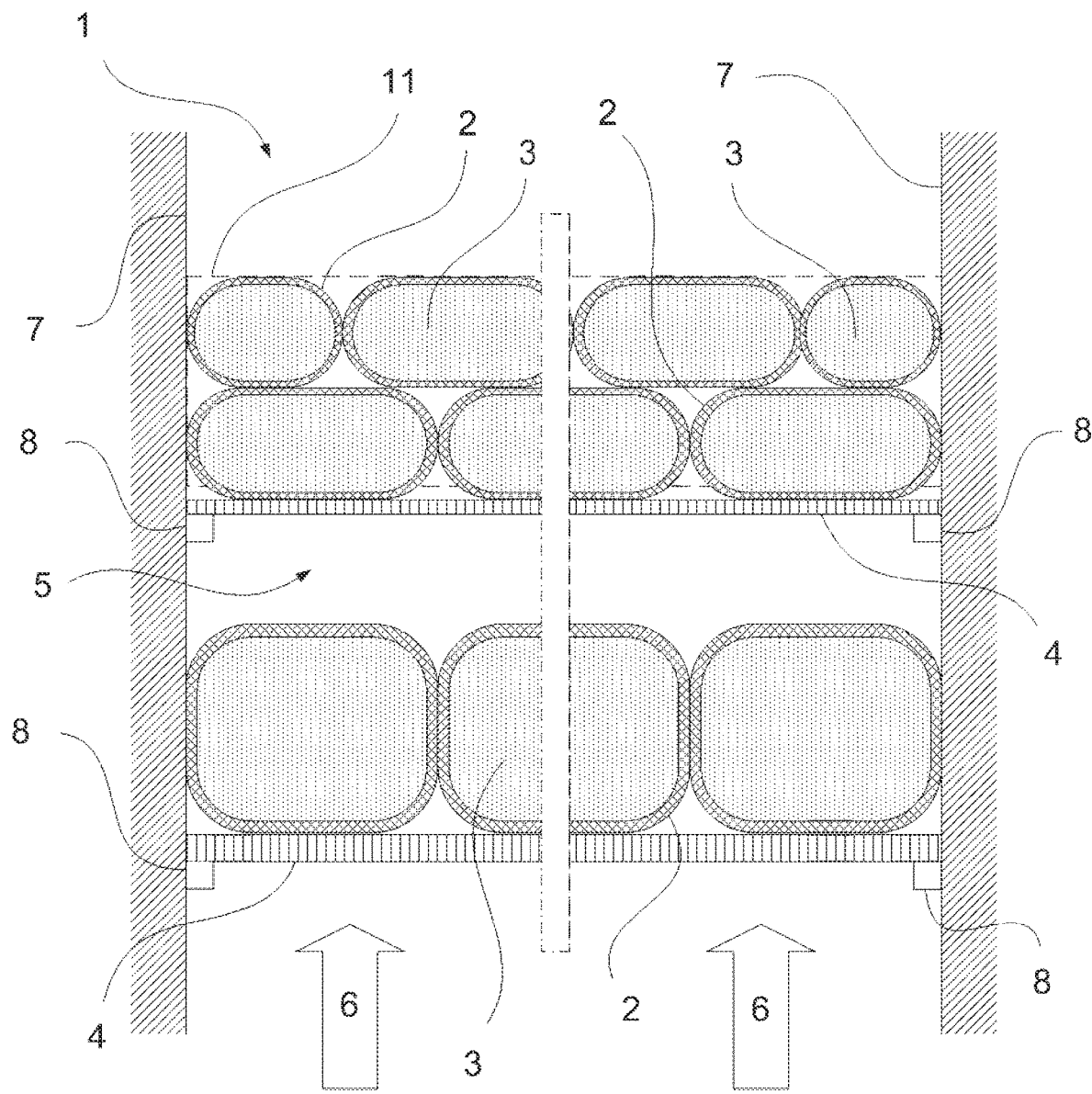
FIG. 4 is a section of an embodiment of the filter module having a plurality of layers of containers on a single support.

Although favorable the scope of the invention must not be limited by the embodiments presented but contain also embodiments obvious to a person skilled in the art. For instance the bag material may comprise a woven cloth or a metal net. All material capable of holding the activated adsorbent and yet letting the gas flow through may be acceptable. The layer of active adsorbent bags may comprise bags of different sizes and shapes. Each layer may comprise a plurality of layers of active adsorbent bags (FIG. 4). The adsorbent may comprise any material that is capable of adsorbing odor or poisonous gas particles.

The invention claimed is:

1. A filter system for adsorbing molecules from a gas, comprising:
   a filter module having opposing inner walls and an inlet and an outlet;
   a plurality of layers of formable gas-permeable containers arranged in the filter module on a first support, and perpendicular to a flow of the gas between the inlet and the outlet;
   wherein the containers contain an active adsorbent, and are arranged in close proximity to each other; and
   wherein the plurality of layers of containers configured to fill a space between the opposing inner walls.

2. The filter system according to claim 1, wherein the first support is a diffuser or a grid.

3. The filter system according to claim 1, further comprising at least one layer of gas-permeable containers containing an active adsorbent arranged on a second support.

4. The filter system according to claim 1, wherein the containers are made from a woven material.

5. A method of adsorbing molecules from a gas, comprising:
providing a filter module having opposing inner walls and an inlet and an outlet, the filter module comprising a plurality of layers of formable gas-permeable containers arranged in the filter module on a first support, and perpendicular to a flow of the gas between the inlet and the outlet, wherein the containers contain an active adsorbent, and are arranged in close proximity to each other, and wherein the plurality of layers of containers is configured to fill a space between the opposing, inner walls; and
passing the flow of the gas containing the molecules from the inlet to the outlet to allow the active adsorbent to adsorb the molecules.

6. The method according to claim 5, wherein the containers are made from a woven material.

7. The filter system according to claim 1, wherein the molecules are poisonous molecules, or odor-causing molecules.

8. The filter system according to claim 1, wherein the containers are sacks or bags.

9. The method according to claim 7, wherein the molecules are poisonous molecules or odor-causing molecules.

10. The method according to claim 7, wherein the containers are sacks or bags.

11. The method according to claim 5, further comprising:
arranging at least one layer of gas-permeable containers filled with an active adsorbent in the filter module on a second support in the filter module;
wherein the at least one layer of containers on the second support is arranged parallel to the plurality of layers of containers on the first support, and is separated from the plurality of layers of containers by a cavity.

* * * * *